(12) United States Patent
Hermans et al.

(10) Patent No.: US 10,957,441 B2
(45) Date of Patent: Mar. 23, 2021

(54) APPARATUS FOR DISPLAYING IMAGE DATA ON A DISPLAY UNIT BASED ON A TOUCH INPUT UNIT

(71) Applicant: KONINKLIJKE PHILIPS N.V., Eindhoven (NL)

(72) Inventors: Ronaldus Petrus Johannes Hermans, Heeze (NL); Adrie Baselmans, Waalre (NL); Ivo Don Stuyfzand, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 65 days.

(21) Appl. No.: 15/764,356

(22) PCT Filed: Sep. 30, 2016

(86) PCT No.: PCT/EP2016/073378
§ 371 (c)(1),
(2) Date: Mar. 29, 2018

(87) PCT Pub. No.: WO2017/055523
PCT Pub. Date: Apr. 6, 2017

(65) Prior Publication Data
US 2018/0275836 A1    Sep. 27, 2018

(30) Foreign Application Priority Data
Oct. 2, 2015 (EP) .................................... 15188101

(51) Int. Cl.
*G16H 30/20* (2018.01)
*G06F 9/451* (2018.01)
(Continued)

(52) U.S. Cl.
CPC ........... *G16H 30/20* (2018.01); *G06F 3/0481* (2013.01); *G06F 3/0482* (2013.01); *G06F 3/0488* (2013.01); *G06F 3/04886* (2013.01); *G06F 3/04895* (2013.01); *G06F 9/452* (2018.02); *G16H 15/00* (2018.01); *G16H 40/63* (2018.01);
(Continued)

(58) Field of Classification Search
CPC .. G06F 3/04886; G06F 3/0489; G06F 3/1462; G06F 3/038; G06F 3/0482; G06F 3/481; G06F 3/1454; G06F 2203/04803; G06F 3/0481; G16H 30/20
See application file for complete search history.

(56) References Cited

U.S. PATENT DOCUMENTS

2007/0198141 A1    8/2007  Moore
2010/0295788 A1   11/2010  Miller
(Continued)

FOREIGN PATENT DOCUMENTS

EP      2882195 A1    6/2015
JP   2000242383 A    9/2000
(Continued)

*Primary Examiner* — Eric J Yoon

(57) ABSTRACT

An apparatus displays (20) first data on at least one display unit. A user interaction portion of a user input area of at least one input unit is determined (30); and on the at least one display unit a portion of the first data is displayed (40) simultaneously with second image data. The second image data is representative of the user interaction portion of the user input area of the at least one input unit.

8 Claims, 7 Drawing Sheets

(51) Int. Cl.
   *G06F 3/0481* (2013.01)
   *G06F 3/0489* (2013.01)
   *G06F 3/0488* (2013.01)
   *H04N 21/422* (2011.01)
   *G16H 40/63* (2018.01)
   *G16H 15/00* (2018.01)
   *G06F 3/0482* (2013.01)
   *G06F 3/14* (2006.01)

(52) U.S. Cl.
   CPC ..... *H04N 21/42222* (2013.01); *G06F 3/1454* (2013.01); *G09G 2354/00* (2013.01)

(56) References Cited

U.S. PATENT DOCUMENTS

| | | |
|---|---|---|
| 2011/0063224 A1 | 3/2011 | Vexo |
| 2012/0005615 A1* | 1/2012 | Gruber ............... G06F 3/03547 715/773 |
| 2012/0182244 A1 | 7/2012 | Arthur |
| 2013/0194188 A1* | 8/2013 | Walker ................ G06F 3/038 345/168 |
| 2014/0275844 A1 | 9/2014 | Hoseit |
| 2014/0276056 A1* | 9/2014 | Ohta ..................... A61B 6/465 600/440 |
| 2016/0054901 A1* | 2/2016 | Yang ................. G06F 3/04845 |

FOREIGN PATENT DOCUMENTS

| | | | |
|---|---|---|---|
| JP | 2006209381 A | 8/2006 | |
| JP | 2007233459 A | 9/2007 | |
| WO | 2014112095 A1 | 7/2014 | |
| WO | WO2015027108 * | 2/2015 | ............ G09B 15/00 |

\* cited by examiner

APPARATUS FOR DISPLAYING IMAGE DATA ON A DISPLAY UNIT BASED ON A TOUCH INPUT UNIT

CROSS-REFERENCE TO PRIOR APPLICATIONS

This application is the U.S. National Phase application under 35 U.S.C. § 371 of International Application No. PCT/EP2016/073378, filed on Sep. 30, 2016, which claims the benefit of European Patent Application No. 15188101.8, filed on Oct. 2, 2015. These applications are hereby incorporated by reference herein.

FIELD OF THE INVENTION

The present invention relates to an apparatus for displaying data, and to a method for displaying data, as well as to a computer program element and a computer readable medium.

BACKGROUND OF THE INVENTION

In certain medical applications, for example those involving a medical imaging system such as an interventional X-ray system, there is a need for a user to operate a graphical user interface (GUI) on an input device such as a touch device, while viewing a different screen of a display device. However, if the user needs to activate certain functionality through the GUI on the input device, they need to look away from the screen of the display device, activate a button corresponding to the required functionality on the GUI of the input device, and then look back at the display device to judge the result of the action. Similar issues apply when a user interacts with an input unit in non-medical applications, such as when using a TV remote control whilst watching the television.

US 2012/0182244 A1 relates to systems and methods for providing remote assistance with a medical procedure by a technician via a remote device such as a laptop or tablet. Video output generated by medical devices and video captured by camera, may be transmitted via a network and rendered on the remote device.

However, the user may still not be provided with the necessary feedback regarding how images or other data are being displayed.

SUMMARY OF THE INVENTION

It would be advantageous to have an improved technique for displaying data in particular for a medical imaging system such as an interventional X-ray system.

According to a first aspect, there is provided an apparatus for displaying data, comprising:
  at least one display unit;
  at least one touch input unit comprising a display screen configured to display input unit image data representing a graphical user interface of a user input area, the graphical user interface comprising a plurality of zones; and
  a processing unit;
  wherein, the processing unit is configured to display first image data on the at least one display unit;
  wherein, the processing unit is configured to determine, as a user interaction portion of the user interface, a zone of the plurality of zones with which the user is interacting, and wherein, the processing unit is configured to display, on the at least one display unit, the first image data simultaneously with second image data being representative of the user interaction portion of the graphical user interface.

In other words, a user can interact with a touch input device and on a separate display device be provided with visual feedback about the area of the touch device user interface that the user is interacting with. To put it another way, a user gets direct feedback on a display unit (such as a viewing device) of the part of a graphical user interface on an input unit (such as a touch device) they are interacting with.

In this manner, a user does not need to look away from the display unit with respect to interacting with the input unit. In other words, in an example, blind touch screen control is provided with feedback about the area of the touch device user interface that a user is interacting with being provided to the user. To put it another way, improved interaction feedback is provided, when interacting on an input unit such as a touch while looking at a separate display unit for interaction feedback.

Preferably, only a single zone or panel of the graphical user interface (GUI) on the input unit is represented on the at least one display unit. Thereby, the amount of screen area on the at least one display unit required to represent the touch device GUI is limited. Preferably, the second image data corresponds to the image data representing the graphical user interface for the active zone, that is the zone with which the user is interacting. Thus, the contents of the active zone of the GUI are mirrored on the main display.

Advantageously, only a limited amount of space is taken up on the screen of the at least one display unit, and the space that is taken up is directly related to what the user is doing on the touch device. In other words, space on the at least one display unit is efficiently and effectively being used. To put it another way, because second image data of a touch device that is representative of the user interaction portion of the user input area of the touch device is shown on a viewing device, the amount of screen area on the viewing device to be dedicated to mirroring, or showing a schematic representation of, the touch device user interface is limited.

In other words, if an input unit such as a touch screen is showing imagery that is already being presented on the at least one display unit, the imagery is not duplicated on the display device.

In an example, the first data comprises a further graphical user interface and the second image data comprises a portion of the touch screen graphical user interface, and the second image data is rendered next to a portion of the further graphical user interface.

Alternatively, the second image data is blended with a portion of the further graphical user interface. In a further alternative embodiment, the second image data is rendered inside a portion of the first graphical user interface.

In an example, the processing unit is configured to determine the user interaction portion when a user moves a hand over at least one zone of the plurality of zones of the graphical user interface.

Alternatively or in addition, the processing unit is configured to determine the user interaction portion when a user touches at least one zone of the plurality of zones of the graphical user interface.

Alternatively or in addition, the processing unit is configured to determine the user interaction portion when a pointer moves over at least one zone of the plurality of zones of the graphical user interface.

In this manner, the position of for example a cursor as shown on an image displayed on a touch device can now be presented on a separate viewing device which shows a portion of the image shown on the touch device along with the cursor position. In other words, the user can keep track of where a cursor is located on a touch screen whilst looking at a separate viewing screen. To put it another way, when an input unit (e.g. touch device) user interface or graphical user interface shows different content to that shown on at least one display unit (e.g. viewing device), it can be unclear where a pointing device is located on the touch screen user interface if a user had to look at the touch device and attempt to locate a cursor within a complex image background. However, by providing a localized user interaction portion, e.g. a cursor position, as part of the second image data presented on the viewing device, the user is better able to keep track of where the cursor is located on the touch device and can do so without having to look away from the viewing device.

In an example, display of the second image data on the at least one display unit is enabled or disabled as a function of input from the user.

According to a second aspect, there is provided a medical imaging system, such as an interventional X-ray system, comprising an apparatus for displaying data in accordance with the invention. The display unit is preferably provided as an overhead monitor, for example an exam room monitor, and the touch input device is preferably provides as a table side module (TSM), that is a control device arranged adjacent to a patient table.

According to a third aspect, there is provided a method for displaying data, comprising:
a) displaying first image data on at least one display unit;
b) determining, as a user interaction portion of a graphical user interface, a zone of a plurality of zones of the graphical user interface with which the user is interacting; and
c) displaying on the at least one display unit, a portion of the first data simultaneously with second image data, the first image data simultaneously with second image data being representative of the user interaction portion of the graphical user interface.

According to another aspect, there is provided a computer program element for controlling an apparatus as previously described which, when the computer program element is executed by a processing unit, is adapted to perform the method steps as previously described.

According to another aspect, there is provided a computer readable medium having stored the computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
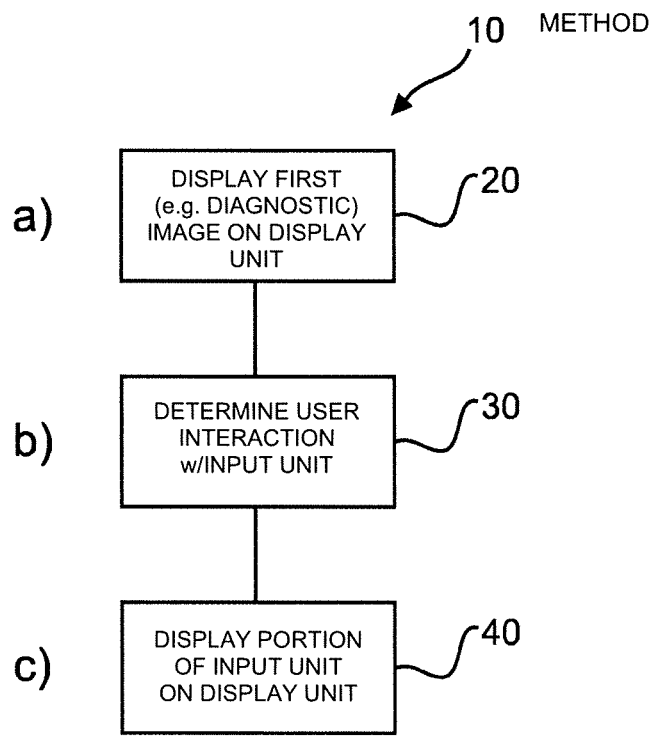
FIG. 1 shows an example of a method for displaying data.

FIG. 1 shows a method 10 for displaying data in its basic steps, the method 10 comprising:
In a first displaying step 20, also referred to as step a), first data is displayed on at least one display unit.
In a determining step 30, also referred to as step b), a user interaction portion of a user input area of at least one input unit is determined.
In a second displaying step 40, also referred to as step c), on the at least one display unit a portion of the first data is displayed simultaneously with second image data, wherein the second image data is representative of the user interaction portion of the user input area of the at least one input unit.

In an example, the first data comprises image data. In an example, the first data comprises text data. In an example, the first data comprises signals. In an example, the first data comprises any combination of these data. For example, in an example the first data comprises image and text data.

Figure 2:
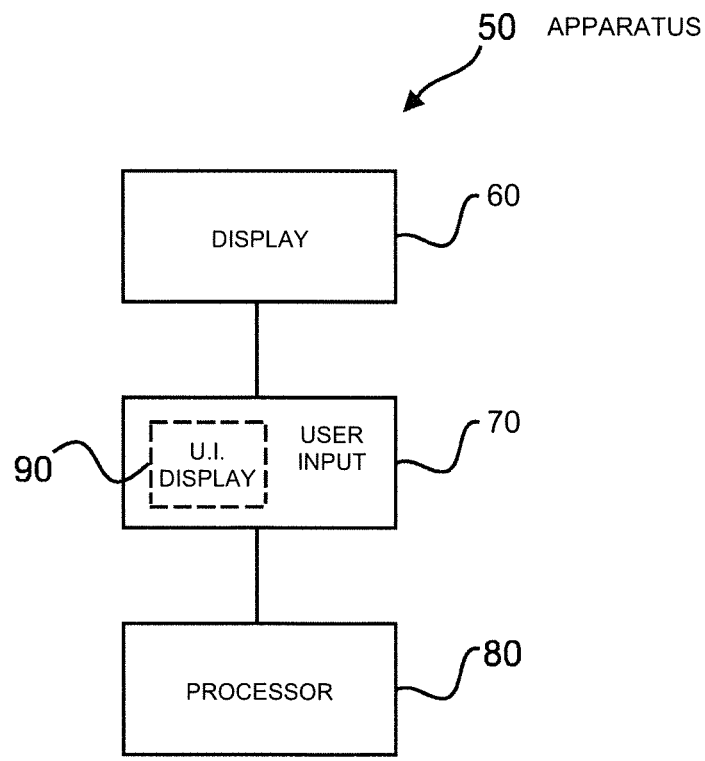
FIG. 2 shows a schematic set up of an example apparatus for displaying data.

FIG. 2 shows an apparatus 50 for displaying data. The apparatus 50 comprises at least one display unit 60, at least one input unit 70 comprising a user input area, and a processing unit 80. The processing unit 80 is configured to display first image data on the at least one display unit 60. The processing unit 80 is also configured to determine a user interaction portion of the user input area of the at least one input unit 70. The processing unit 80 is also configured to display on the at least one display unit 60 a portion of the first image data simultaneously with second image data, wherein the second image data is representative of the user interaction portion of the user input area of the at least one input unit 70.

In an example, the at least one display unit comprises a monitor configured to display medical image data, preferably an overhead monitor as may be arranged inside a hospital examination room. In an example, the first data comprises interventional X-ray data. In an example, the first data comprises CT X-ray image data, X-ray fluoroscopic image data, X-ray tomography image data, Magnetic Resonance (MR) image data, ultrasound image data or any combination of these image data.

In an example, the at least one touch input unit comprises a device with a screen that a user can touch, such as a smartphone or tablet PC, or in a preferred embodiment a table side module adjacent to a patient table in a hospital examination room. A user may be interacting with the touch input device while looking at an overhead display preferably showing a graphical user interface of the touch device. For example, a tablet user interface or graphical user interface can be directly rendered on the screen In an example, the at least one input unit can be a touch device with its own graphical user interface, such as a touch device showing separate processing, acquisition, medical device configuration and measurement functionalities relating to medical imagery presented on a separate display unit, and the processing unit can determine the area of the touch device a user is interacting with such as that relating to measurement functionalities and present the measurement functionalities as shown on the touch pad as a separate, or integrated, region on the at least one display unit along with the medical image data. However, even though the input unit can have a display screen this does not necessarily mean that the second image data representative of the user interaction portion of the user input area of the input unit is mirroring image data presented on the input unit. Representative here means that, even if the input unit is showing imagery, the display unit could show schematic representations of that imagery. However, representative also means that the display unit could mirror at least a portion of what is being shown on a display screen of an input unit.

In an example, the at least one input unit comprises a device configured to detect the proximity of a user's hand or pointer or stylus without the user having to touch the input unit with their hand or pointer or stylus. For example, the at least one input unit can utilize microwave or laser sensing to determine the proximity to and location of the user's hand with respect to a user input area of the input unit in order to determine the user interaction portion. In an example, the at least one input unit detects the proximity and location of a user's had with respect to the input unit using a camera viewing the user's hand. In an example, the at least one input unit detects the proximity and location of a user's hand with respect to the input unit through magnetic field disturbance sensing of the user's hand. In other words, the at least one input unit can be a touch device and/or a proximity device.

In other words, in an example there can be multiple display units and/or multiple input units. For example with respect to multiple display units, there can be a display unit in a Control Room and a display unit in an Exam Room. For example with respect to multiple input units, there can be an input unit (such as a Table Side Module) for a physician (close to a patient) and there can be an input unit for a nurse.

In an example, the second image data is a direct reproduction of the image data representing at least an active portion of a graphical user interface that the user is interacting with. For example, the input unit can be a touch device with its own screen on which there is a first zone or area showing medical imagery and a second zone or area showing buttons relating to control or processing of that medical imagery.

The at least one display unit can be a medical exam room monitor displaying an enlargement of the imagery as shown on the at least one input unit, and when the user interacts with the input unit at the location of the buttons, imagery of the buttons as presented on the input unit can be mirrored on the at least one display unit.

In an example, as a user's finger approaches the input unit (e.g. touch device) the part of the image being presented on the touch device centered around the location of the finger, which may not have touched the touch device yet, is presented on the at least one display unit (e.g. viewing device). In this manner, the user may move their finger towards the center right of the screen of a touch device. On the touch device there may be an image being presented on the center of the screen that is shown in expanded form on the viewing device, and a number of functional buttons may be presented on the far right of the touch screen. In this case, as the user's finger approaches the touch screen the user is presented on the viewing device with an image portion from the touch device with parts of buttons being shown. As they move their finger to the right over the touch screen, the image on the viewing device shows less of the image as presented on the touch device and more of the buttons on the touch device. Finally, the user is presented with information on the viewing device regarding the touch device presented as required, such as the functional buttons, enabling the user to press the button on the touch device that they wish to press. In this manner, they can interact with the imagery presented on at least one display unit via interacting with a separate input unit without having to move their line of sight away from the at least one display unit.

According to an example, as shown in FIG. 2, the at least one input unit 70 comprises a display screen 90 configured to display input unit image data, wherein the user input area of the at least one input unit 70 comprises at least a portion of the input unit image data displayed on the display screen, and wherein the second image data comprises at least a portion of the input unit image data.

In an example, the user input area of the at least one input unit comprising at least a portion of the input unit image data displayed on the display screen means that the user input area of the at least one input unit displays at least a portion of the input unit image data.

In other words, in an example a part of a user interface or graphical user interface of an input unit (e.g. a touch device) is rendered on the at least one display unit (e.g., viewing device). Preferably, the part is an active zone, that is, one of a plurality of zone of the graphical user interface with which a user is interacting.

In an example, the input unit image data comprises interventional X-ray data. In an example, the input unit image data comprises CT X-ray image data, X-ray fluoroscopic image data, X-ray tomography image data, Magnetic Resonance (MR) image data, ultrasound image data or any combination of these image data. In an example, the input unit image data comprises image relating to button functionalities for the processing and/or acquisition of medical image data and/or control of equipment associated with the acquisition of image data, such as an X-ray unit or MRI unit. For example, the input unit image data can relate to buttons having functionalities including any combination of: acquisition; X-ray unit control and/or medical table control; X-ray beam collimation; processing; zoom & pan; contrast & Brightness; subtraction; measurements; image overlays; reset; and the opening of files.

In an example, the at least one input unit comprises a touch screen and a portion of the graphical user interface or user interface that the user is touching or has touched is represented in schematic form on the at least one display unit. In an example, the at least one input unit comprises a touch screen and a portion of the graphical user interface or user interface that the user is touching or has touched is mirrored on the at least one display unit. In other words, a subset of the imagery being shown on the input device, such as a touch screen device, can be rendered on the display device, or a schematic representation of that imagery on the input device can be presented on the display device.

In an example, the at least one input unit comprises a proximity device having a screen and a portion of the graphical user interface or user interface that the user is in proximity with or has been in proximity with is represented in schematic form on the at least one display unit. In an example, the at least one input unit comprises a proximity device having a screen and a portion of the graphical user interface or user interface that the user is in proximity with or has been in proximity with is mirrored on the at least one display unit.

According to an example, if the input unit image data comprises at least a portion of the first data, the processing unit is configured to display the second image data without displaying any first data, as displayed on the at least one input unit, as part of the second image data.

In other words, if an input unit such as a touch screen is showing imagery that is already being presented on the at least one display unit, the imagery is not duplicated on the display device. For example, image A can be presented on a display unit and image B can be shown on an input unit along with a number of functional buttons on the right hand side of the screen. If the user is interacting with the buttons at the top right of the screen then these buttons, along with the portion of image B near or around those buttons, can be displayed on the display unit along with image A. However, if the input unit was showing image A rather than image B, then only the buttons at the top right hand side of the input unit that the user is interacting with are displayed on the display unit. In this manner, redundant data is not presented to the user. In other words, if an image of a vascular region of a patient is shown on the screen of an input unit (e.g. touch device) and the same image at the same level of magnification is being shown on the display unit (e.g. viewing device) then the vascular image data from the touch device is not reproduced on the viewing device, and only the other image data that the user is interacting with such as that relating to buttons with image manipulation functionalities. In an example, if the same image data is shown on the at least one input unit as shown on the display unit, but at a different level of magnification, then it may be reproduced on the display unit if the user is interacting at that region of the input unit.

According to an example, the user input area comprises a plurality of zones, and wherein the user interaction portion of the user input area comprises at least one zone.

In an example, only a zone of the user interface or graphical user interface of the at least one input unit, such as a touch device or proximity device, that a user is interacting with, is rendered on the at least one display unit such as a viewing device. In an example, a zone is equivalent to a panel on the input device.

According to an example, the first data comprises a first graphical user interface and the second image data comprises a portion of a second graphical user interface, and wherein the portion of the second graphical user interface is rendered next to a portion of the first graphical user interface.

In other words, the portion of imagery on the input device that the user is interacting with can be shown on the display device next to either all of what was being shown on the display device or next to most of what was being shown. In other words, the original imagery can be resized in order to present the new imagery next to the old imagery, or the new imagery can be overlaid over one side of the old imagery.

According to an example, the first data comprises a first graphical user interface and the second image data comprises a portion of a second graphical user interface, and wherein the portion of the second graphical user interface is blended with a portion of the first graphical user interface.

In an example, the amount of blending is dependent upon the distance of a pointing device to the input device. For example, as a user's finger approaches the input unit (such as a touch device) the region of the touch device centered around the location of the finger (above the screen) is presented on the at least one display unit (e.g. viewing device). In an example, as the user's finger approaches or recedes from the touch device screen, the image from the touch device presented on the viewing device becomes brighter and fades accordingly.

According to an example, the first data comprises a first graphical user interface and the second image data comprises a portion of a second graphical user interface, and wherein the portion of the second graphical user interface is rendered inside a portion of the first graphical user interface.

In other words, the positioning of the second image data, such as a portion of what is being presented on a touch screen and represents or mirrors the content of the touch screen the user is interacting with, can be controlled or adjusted as required.

According to an example, the processing unit is configured to determine the user interaction portion when a user moves a hand over at least one portion of the user input area of the at least one input unit.

For example, the processing unit determines that the user has moved their hand over the right hand portion of the touch screen of an input unit, and the buttons and/or image data shown at the right hand portion of the touch screen is displayed on the at least one display unit along with at least a portion of the image data that was already being displayed on the at least one display unit. In an example, a user can be simultaneously hovering their hand over multiple zones, e.g., the left hand area and the right hand areas of a touch/proximity device.

According to an example, the processing unit is configured to determine the user interaction portion when a user touches a portion of the user input area of the at least one input unit.

For example, the processing unit determines that the user has touched the right hand portion of the touch/proximity screen of an input unit, and the buttons and/or image data shown at the right hand portion of the touch screen is displayed on the at least one display unit along with at least a portion of the image data that was already being displayed on the at least one display unit.

According to an example, the processing unit is configured to determine the user interaction portion when a pointer moves over a portion of the user input area of the at least one input unit.

In an example, the pointer comprises a cursor displayed on the user input area of the at least one input unit. For example, the processing unit determines that the user has moved the cursor over the right hand portion of the screen of an input unit, and the buttons and/or image data shown at the right hand portion of the touch screen is displayed on the at least one display unit along with at least a portion of the image data that was already being displayed on the at least one display unit.

According to an example, the processing unit is configured to determine a localized user interaction position of the user interaction portion, and wherein the second image data comprises image data representative of the localized user interaction position.

In an example, a localized interaction position comprises a position of a cursor displayed on the user input area of the at least one input unit.

According to an example, display of the second image data on the at least one display unit is enabled or disabled as a function of input from the user.

In this manner, the required functionality can be enabled/disabled as necessary, for example based on a user's hand approaching, touching or being removed from the input unit, such as a touch device or proximity device, or based on other input from the user. In an example, the input from the user comprises a button or pedal being depressed. In an example, the input from the user comprises a duration in time of input from the user. In other words, a threshold in time can apply and if the input from the user, such as the user's hand being in a particular position, exceeds a certain time then the display of second image data on the at least one display unit is enabled.

In an example, it is possible to have more than one display unit. In an example, it is possible to have more than one input unit. In an example, it is possible to have more than one display unit and more than one input unit.

Figure 3:
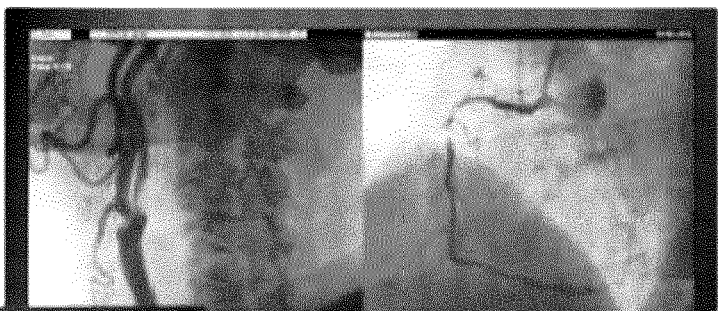
FIG. 3 shows an example of an input unit, and two display units.
Figure 3:
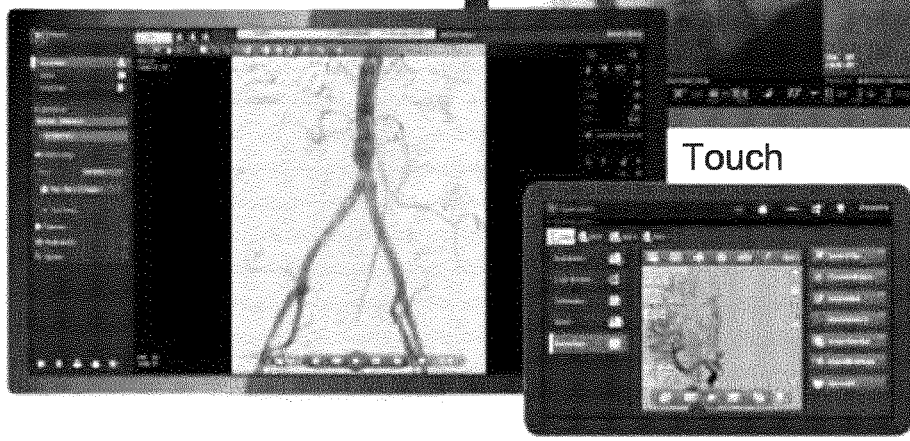

FIG. 3 shows an input device in the form of a touch device, shown at the bottom and labelled as "Touch", and two display devices in the form of a desktop and viewing device, shown at the middle and top and labelled as "Desktop" and "Viewing". The display devices are showing enlarged portions of what is being shown on the touch device. This arrangement represents an approach in which one or more viewing devices are used for main visual feedback and a touch device is used for interaction purposes. The touch device can have its own user UI or GUI (e.g. a phone) or have no UI or GUI (e.g. a mouse pad or TV remote control). In this approach, while interacting on a touch device, the user gets no direct visual feedback on the viewing device as to where on the touch device interacting. For example, as shown in FIG. 3 when the touch device has a UI or GUI and the UI or GUI shows a different content than the content being displayed on the UI or GUI of the viewing device, it may be unclear or difficult to determine where a pointing device, such as a cursor, is located on the UI or GUI of the touch device. In the current approach, large buttons are placed on the touch device at positions that are easily found by hand interaction, as represented on the screen of the touch device shown in FIG. 3. However, the user needs to look on the touch device to find the functionality of interest (e.g. a button) and after pressing the button or positioning the cursor over the button and clicking the user must then look back to the viewing device to judge the result.

The apparatus and method for displaying data of the present disclosure is applicable to a wide variety of device setups. For example:

Interacting on a mobile phone or tablet (touch device) while looking at a television (viewing device) that shows the UI of the touch device. For example a tablet UI that serves as a remote control UI can be directly rendered on the television. Interacting on a Table Side Module (touch device) of an X-ray device while looking at the exam room screen (viewing device) that shows the X-ray images.

Figure 4:
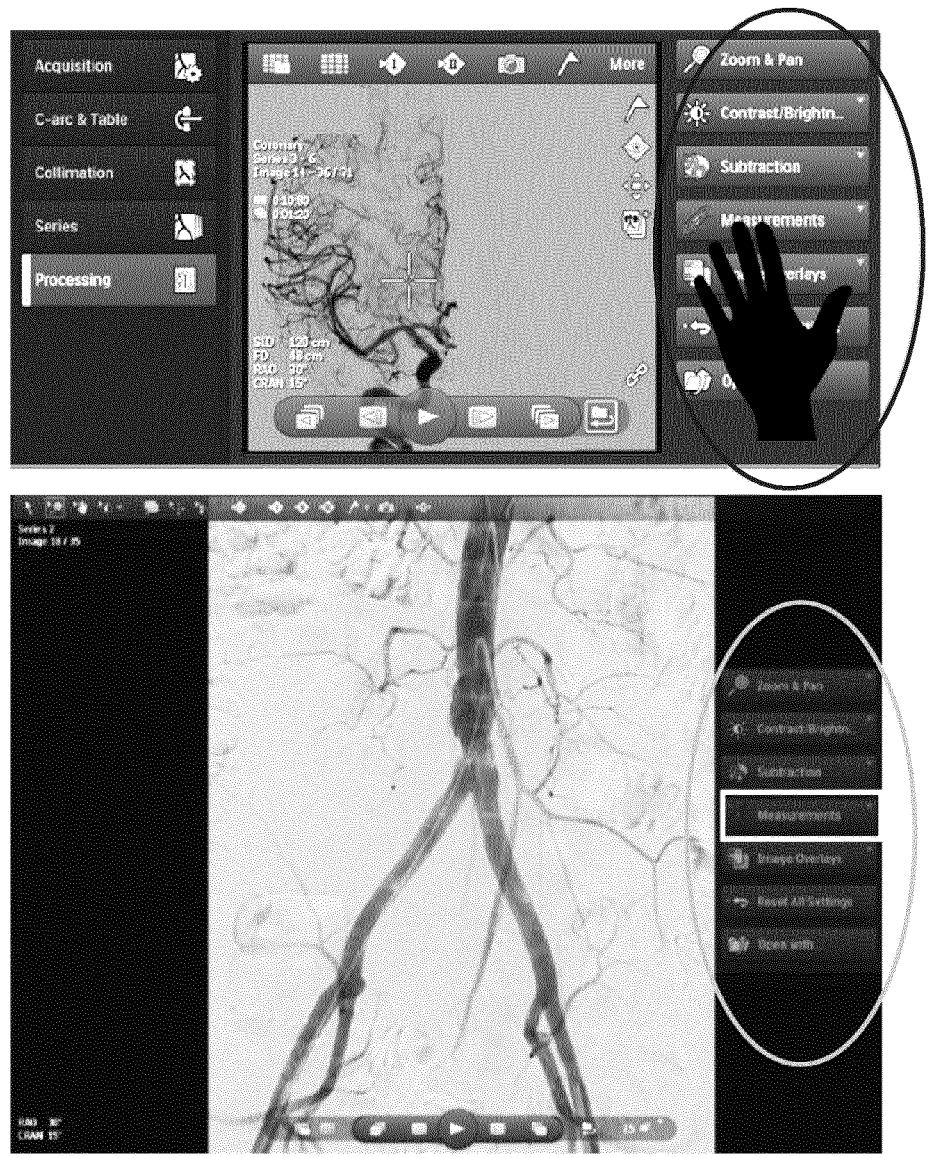
FIG. 4 shows an example of data being displayed by an example apparatus for displaying data.
Figure 5:
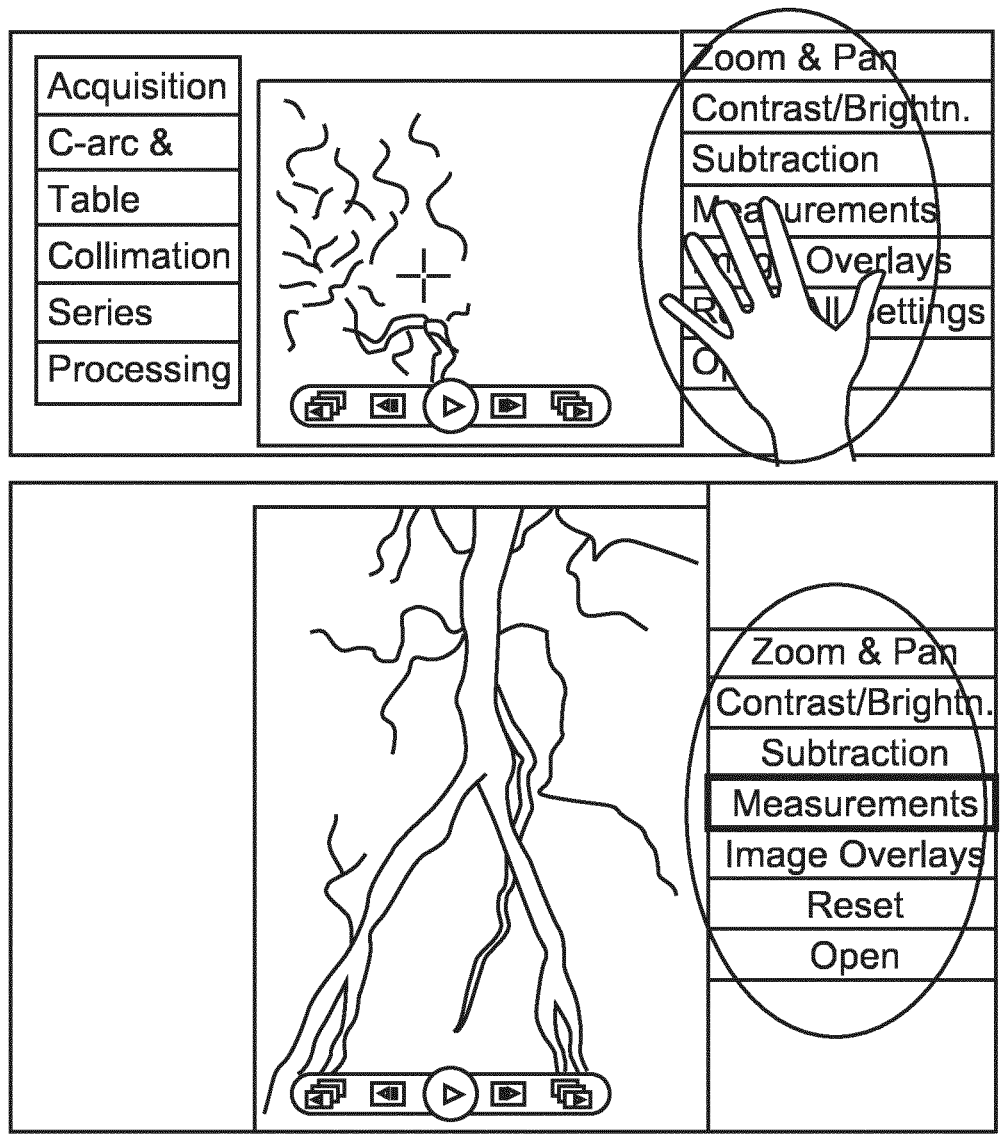
FIG. 5 shows the same data as shown in FIG. 4, represented in schematic form.

For example, the apparatus and method can be used in the following cases: Use case 1, which is represented in FIG. 4 and FIG. 5 which show an example of data being displayed by an example apparatus of the present disclosure for displaying data. In FIG. 4 and FIG. 5, an input unit in the form of a touch device having a UI is shown in the top image, and a display unit in the form of a viewing device having a UI is shown in the bottom image. In summary, when a user's hand comes over the right-hand side of the touch device UI this part of the touch device UI, that is, the right panel or right zone, is blended in the viewing device UI. Furthermore, optionally, in the viewing device UI the button over which the user's hand is hovering or the button being touched on the touch device UI is highlighted. In more detail, for the situation where the input unit is a Table Side Module (TSM) and the display unit is an exam room monitor:

User moves his hand over the buttons in the right panel of the Table Side Module (TSM).

A rendering of the panel UI showing the buttons is displayed on the exam room monitor and optionally directly shows over which button the user is hovering (or touching).

User presses the button and can directly see the effect on the X-ray image on the exam room monitor.

User moves hand away from Table Side Module.

The panel UI rendering disappears from the exam room monitor, leaving a clean, non-distracting UI in the exam room.

Figure 6:
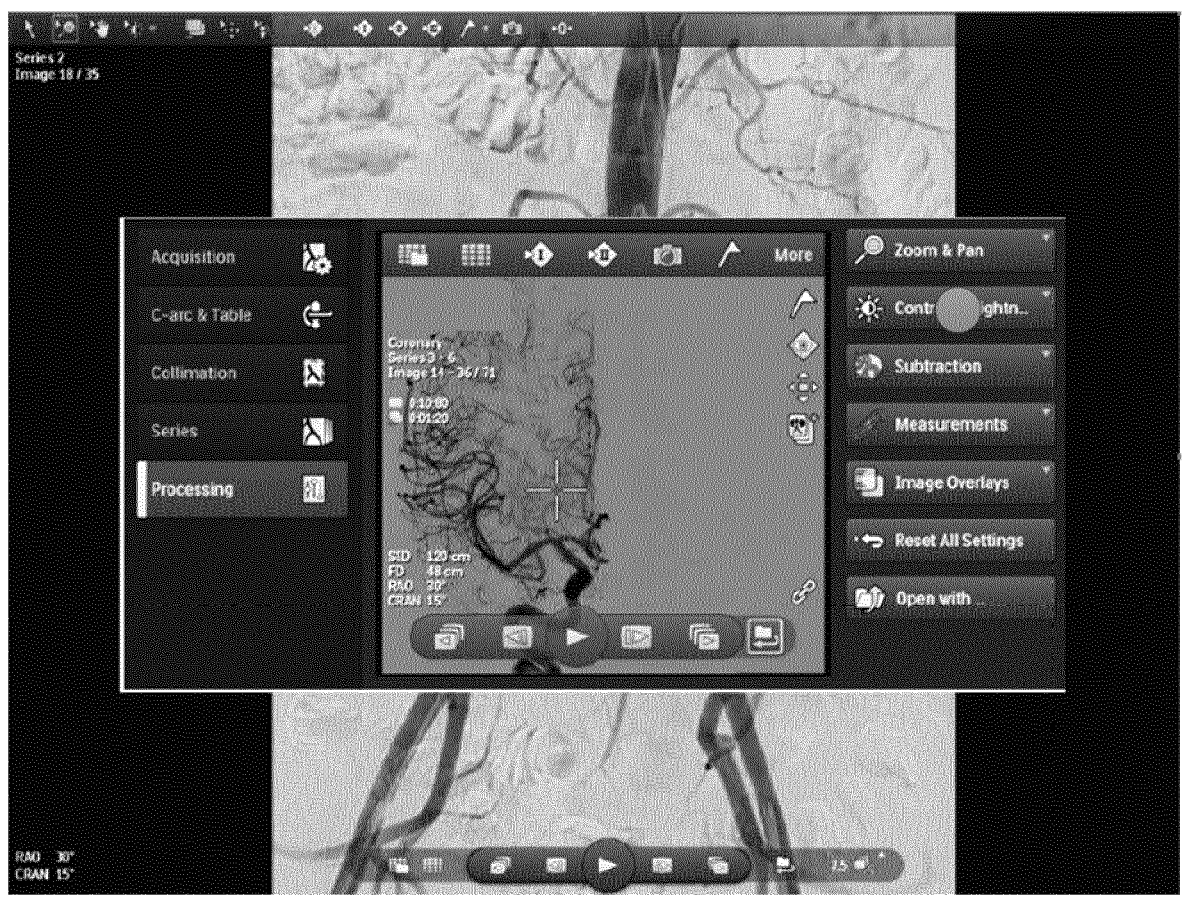
FIG. 6 shows an example of data being displayed by an example apparatus for displaying data.
Figure 7:
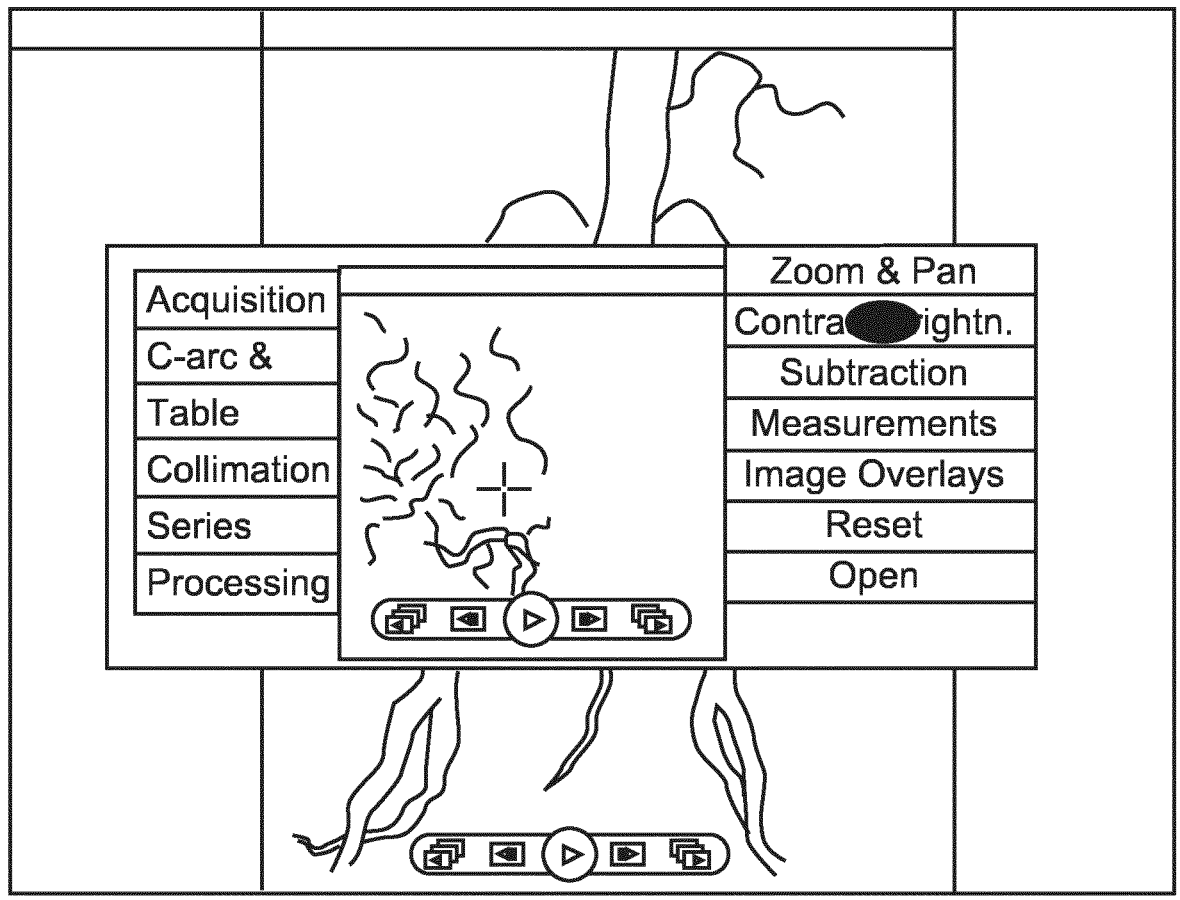
FIG. 7 shows the same data as shown in FIG. 6, represented in schematic form.

Use case 2, which is represented in FIG. 6 and FIG. 7 which show an example of data being displayed by an example apparatus of the present disclosure for displaying data. In FIG. 6 and FIG. 7, an input unit (not shown) in the form of the touch device having a UI is showing imagery as shown for the input unit of FIG. 4 and FIG. 5. In FIG. 6 and FIG. 7 a display unit in the form of a viewing device having a UI is shown. In summary, upon an appropriate indication from the user the whole of the UI of the touch device is shown on top of the viewing device UI. In another arrangement, upon an indication of the user the subset of the touch device as discussed above with respect to FIG. 4 and FIG. 5 is shown on top of the viewing device UI, and again the specific button being interacted with by the user can be identified. In more detail, for the situation where the input unit is a Table Side Module (TSM) and the display unit is an exam room monitor:

User presses a pedal/button.

In the exam room the UI of the TSM application renders the TSM UI fully on top of the X-ray viewer application on the exam room monitor.

The position of finger is indicated with clear pointer (see FIG. 6 and FIG. 7, where a circular shaded dot is presented over the Contrast/Brightness functional button).

User releases pedal.

The exam room monitor shows X-ray viewer application.

With respect to the apparatus and method for displaying data according to the present disclosure, multiple embodiments are possible:

The positioning of the UI of the touch device within the UI of the viewing device can be adjusted as follows. The UI of touch device Can be rendered directly next to the UI of the viewing device.

Can be blended with the UI of the viewing device. The amount of blending can be dependent on the distance of the pointing device to the touch device.

Can be rendered inside the UI of the viewing device.

The content of the UI of the touch device can be partially in the UI of the viewing device to reduce the amount of screen area needed for the feedback. This can depend on the position of the pointing device with respect to the touch device UI, e.g. show only buttons from left panel when pointing device is at left, and from right panel when pointing device is at right. See FIG. 4 and FIG. 5.

The rendering of the touch device UI on the viewing device can be: Enabled/Disabled via a hardware or software switch that enables rendering of the touch device UI on the viewing device.

Enabled/Disabled by duration of proximity or contact of the pointing device with the touch device.

In general, the rendering of different UIs of a single application can be implemented by:

Running the logic and rendering of the UI on a computer program (process).

Streaming the rendered results to the different UI devices.

This allows for handling interaction in a central process and distributing the rendered results to different UI devices.

In general, it is possible to have multiple display units (e.g. viewing devices) and multiple input units (e.g. touch devices).

Figure 8:
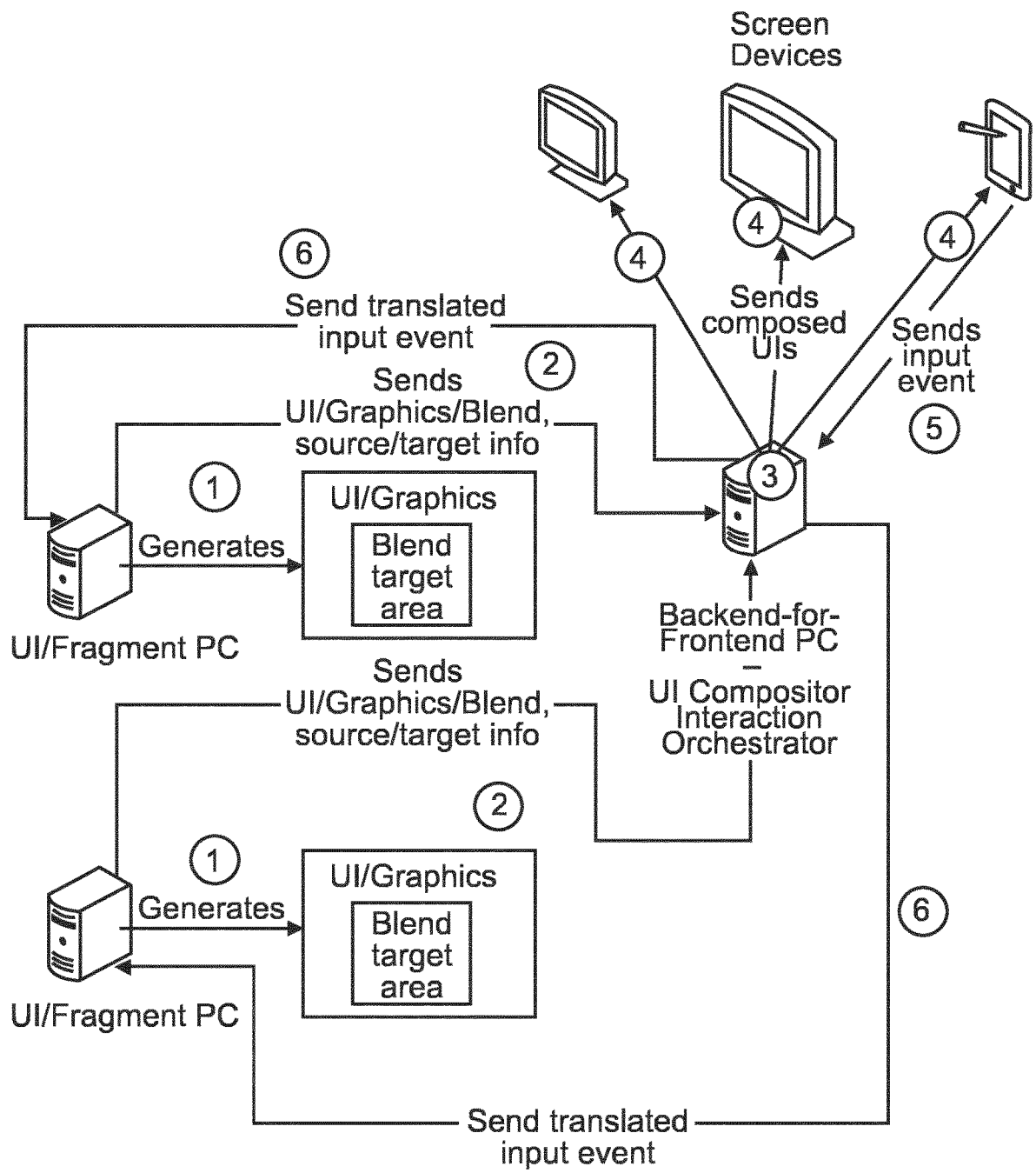
FIG. 8 shows an example of a technical realization of an example apparatus for displaying data with an example workflow.

FIG. 8 shows an example of a technical realization of an example apparatus for displaying data with an example workflow. Referring to the physical units shown in FIG. 8 and with reference to the circled numbers 1-6 also as shown in FIG. 8, the example workflow is now explained, where the numbering below relates to the circled numbers in FIG. 8: The UI fragment PC renders a UI fragment and designates certain logical areas in the UI fragment as either blend targets or blend sources. A blend target is a (logical) part of the UI fragment in which another part of UI fragment can be blended. A blend source is a (logical) part of the UI fragment that will be blended into a target. Rendering can be performed using a rendering framework like OpenGL, DirectX, GDI, or developed in-house. UI creation can be accomplished using a third-party UI framework, e.g. WPF, QT, or developed in-house.

The computers send the UI fragment via a stream (this can be video stream like DVI or network stream via UDP) to the Backend-for-Frontend (BFF) PC. There the UI compositor composes the UI fragments.

Via an interface, the UI compositor has information about blend target areas and blend source areas of the different UIs. This interface can be based on several technologies: a RPC API, a REST or HTTP etc. The UI compositor program running on BFF, uses these interfaces to 'link' blend targets and sources.

The UI Compositor has information about the different screen devices. A software program running on the BFF PC can specify how the different UI fragments should be composed and shown on screens.

The Interaction Orchestrator program running on the BFF ensures that all user-interaction on the screen devices are captured.

The Interaction Orchestrator routes back the input events to the relevant UI fragment PC, which can then apply the required logic for interaction handling. The information can is be sent via network stream or via simulated mouse/keyboard events.

In the above example, various arrangements are possible. For example, instead of 2 UI fragment PCs, there can be 1 (or more than 2), and instead of running on a separate BFF PC, the logic for UI composition and Interaction Orchestration could run on one of the UI fragment PCs (i.e. A single PC solution can be provided). Additionally, in the above a PC can be a computer unit or processing unit, and a UI compositor can be a UI compositor computer program for example.

In another exemplary embodiment, a computer program or computer program element is provided for controlling an appropriate system that is characterized by being configured to execute the method steps according to one of the preceding embodiments.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Furthermore, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for displaying data, comprising:
   at least one display unit;
   at least one touch input unit comprising a user input area having a touch display screen configured to display input unit image data including a graphical user interface comprising a plurality of zones, the plurality of zones including an image zone and at least one functional button zone, the at least one functional button zone including an image of an array of function buttons, the at least one touch input unit being configured to determine a location of one of a user's hand, pointer, or stylus relative to the touch display screen; and a processing unit wherein, the processing unit is configured to display first image data on the at least one display unit;

wherein, the processing unit is configured to determine a user interaction portion of the graphical user interface, the user interaction portion being a portion of the plurality of zones to which the location of the one of the user's hand, pointer, or stylus is proximate, the portion of the plurality of zones changing as the one of the user's hand, pointer, or stylus moves, and wherein, the processing unit is configured to display, on the at least one display unit, the first image data simultaneously with second image data corresponding to the input unit image data for the portion of the plurality of zones proximate to the location of the one of the user's hands, pointer, or stylus, the second image data including at least a portion of the image of the function buttons that includes at least one function button that is proximate to the one of the user's hand, pointer or stylus wherein the first image data comprises a further graphical user interface, and wherein the second image data is rendered next to, blended with, or inside a portion of the further graphical user interface, wherein a brightness of the portion of the plurality of zones varies with a distance of the one of the user's hand, pointer, or stylus from the touch display screen such that as the one of the user's hand, pointer or stylus approaches the touch display screen, the portion of the plurality of zones becomes brighter, wherein the at least one display unit is configured as an overhead monitor and the touch input unit is configured as a table side module that is adjacent to a table, wherein the first image data and the input unit image data each include a computerized tomography (CT), x-ray, magnetic resonance (MR), or ultrasound diagnostic image of a patient with different degrees of magnification, and wherein the second image data comprises an indicator indicating which one of the array of function buttons the user is interacting with.

2. An apparatus for displaying data comprising:

a display device configured to display medical diagnostic image data;

an input device including a touch screen configured to display the medical diagnostic image data and an array of function buttons, the input device further configured to sense touching and non-touching proximity of one of a user's hand, pointer, or stylus to the touch screen;

a processor configured to:

provide the medical diagnostic image data to the display device for display thereon as a first medical diagnostic image with a first level of magnification, provide to the touch screen of the input device:

the medical diagnostic image data as a second medical diagnostic image with a second level of magnification and an image of the array of function buttons, receive an input from the input device indicative of a location and proximity of the one of the user's hand, pointer, or stylus to the touch screen, and control the display device to display at least a portion of the image of the function buttons that includes at least one function button of the array of function buttons that is proximate to the one of the user's hand, pointer, or stylus, the at least one function button being next to, overlaid on, or blended with the first medical diagnostic image, the display device displaying the first medical diagnostic image with the first level of magnification together with the second medical diagnostic image with the second level of magnification, wherein a brightness of a portion of a user interface displayed on the touch screen of the input device varies with a distance of the one of the user's hand, pointer or stylus from the touch screen such that as the one of the user's hand, pointer or stylus approaches the touch screen, the portion of the user interface becomes brighter, wherein the displayed portion of the image of the function buttons changes as the one of the user's hand, pointer, or stylus moves relative to the touch screen of the input device, and wherein the first level of magnification is different from the second level of magnification.

3. The apparatus according to claim 2, wherein the display device is an overhead display.

4. The apparatus according to claim 2, wherein the processor is further configured to control how large a portion of the touch screen is displayed on the display device based on a distance between the touch screen and the one of the user's hand, pointer, or stylus.

5. A method for displaying data comprising:

on a touch screen of an input device, displaying a medical diagnostic image with a first level of magnification and an array of function buttons;

adjusting a brightness of a portion of a user interface displayed on the touch screen of the input device based on a distance of one of a user's hand, pointer or stylus from the touch screen such that as the one of the user's hand, pointer or stylus approaches the touch screen, the portion of the user interface becomes brighter; and with a processor, controlling a display device to perform operations, the operations comprising:

controlling the display device to display the medical diagnostic image with a second level of magnification that is different from the first level of magnification, controlling the display device to display the medical diagnostic image with the first level of magnification and at least a portion of the array of function buttons such that the display device displays the medical diagnostic image with two different levels of magnification, and based on an input received from the input device indicative of a current location of the one of the user's hand, pointer, or stylus and a current proximity of the one of the user's hand, pointer, or stylus to the touch screen, control the display device to display indicia of the current location of the one of the user's hand, pointer or stylus and the current proximity of the one of the user's hand, pointer, or stylus to the touch screen, the displayed indicia changing as the one of the user's hand, pointer, or stylus moves relative to the touch screen.

6. The method according to claim 5, wherein the array of function buttons includes function buttons for modifying a display of the display device.

7. The method according to claim 5, wherein the indicia is displayed one of next to the diagnostic image, overlaid on the medical diagnostic image, or blended with the diagnostic image.

8. A non-transitory computer-readable medium including software to control a processor to perform the method of claim 5.

* * * * *